(12) United States Patent
Roa-Espinosa

(10) Patent No.: US 9,730,463 B1
(45) Date of Patent: *Aug. 15, 2017

(54) SEPARATION OF COMPONENTS FROM WHOLE STILLAGE

(71) Applicant: Aicardo Roa-Espinosa, Madison, WI (US)

(72) Inventor: Aicardo Roa-Espinosa, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/341,922

(22) Filed: Nov. 2, 2016

Related U.S. Application Data

(63) Continuation-in-part of application No. 15/155,037, filed on May 15, 2016, now Pat. No. 9,516,891.

(51) Int. Cl.
| | |
|---|---|
| B01D 17/04 | (2006.01) |
| C02F 1/24 | (2006.01) |
| A23J 3/34 | (2006.01) |
| C07K 1/36 | (2006.01) |
| C11B 3/16 | (2006.01) |
| B01D 17/02 | (2006.01) |
| B01D 33/15 | (2006.01) |
| B01D 33/27 | (2006.01) |
| A23K 10/38 | (2016.01) |
| A23K 50/10 | (2016.01) |
| C07K 1/34 | (2006.01) |

(52) U.S. Cl.
CPC ........... *A23J 3/346* (2013.01); *A23K 10/38* (2016.05); *A23K 50/10* (2016.05); *B01D 17/0205* (2013.01); *B01D 17/0214* (2013.01); *B01D 17/047* (2013.01); *B01D 33/15* (2013.01); *B01D 33/27* (2013.01); *C07K 1/36* (2013.01); *C11B 3/16* (2013.01); *C07K 1/34* (2013.01)

(58) Field of Classification Search
None
See application file for complete search history.

(56) References Cited

U.S. PATENT DOCUMENTS

| | | | | |
|---|---|---|---|---|
| 4,186,089 | A * | 1/1980 | Okada | B01D 33/275 210/203 |
| 2010/0166913 | A1* | 7/2010 | Stewart | C10L 5/44 426/54 |
| 2013/0121891 | A1* | 5/2013 | Dieker | B04B 15/06 422/261 |

FOREIGN PATENT DOCUMENTS

WO  WO 2012/145230 A1 * 10/2012

* cited by examiner

*Primary Examiner* — Thomas M Lithgow
(74) *Attorney, Agent, or Firm* — Steven H Greenfield; Greenfield Invention and Patent Consulting, Inc.

(57) ABSTRACT

A multi stage process for separating oil, protein, fiber and clean water from a stream containing whole stillage byproduct from ethanol production is disclosed. In a first step, fibers are separated in a two-step process that includes a plate separator and a press. In a subsequent step, the liquid stream separated from the fibers and contains oil, protein and water is treated with a composition that causes the protein to gel. The liquid stream is then processed in a phase separator that drains the oil by gravity, removes the water by an impeller under pressure and removes the solidified protein using a scroll.

14 Claims, 2 Drawing Sheets

SEPARATION OF COMPONENTS FROM WHOLE STILLAGE

RELATED APPLICATIONS

This is a continuation in part of application Ser. No. 15/155,037 filed on May 15, 2015.

FIELD OF THE INVENTION

The present invention relates to a process of recovering components from the byproducts of the ethanol manufacturing processes. More specifically, the process of the present invention separates a whole stillage stream that is a by-product of ethanol production into four streams: a stream containing predominantly oil, a stream that contains predominantly water, a stream containing predominantly fibers and a stream containing predominantly protein.

BACKGROUND OF THE INVENTION

The ethanol manufacturing process starts by the cleaning and then the dry-milling of maize grains. The ground grains are mixed with water and enzymes (amylases) to produce a mash where starch hydrolysis occurs. This mash is cooked to kill bacteria that produce undesirable lactic acid. Enzymes are added to the mash to transform starch into dextrose (a saccharification step). After saccharification, yeast is added to start the fermentation process, which produces a beer-like material and carbon dioxide ($CO_2$). The beer passes through a continuous distillation column to yield alcohol at the top of the column. The product that remains at the bottom is whole stillage, which in current practice is separated to produce distillers corn oil (DCO) and distillers' grains. Both byproducts are used as energy and protein sources for ruminants and the distillers corn oil can be used a feed stock for biodiesel production. This invention allows the separation of whole stillage into additional streams contain valuable bio-materials mainly fibers, oil and protein. Greater volumes of oil are recovered for use as a biofuel, animal energy source or for cooking. The ability to separate more DCO creates significant carbon reduction when it is converted to biodiesel rather than being used as an animal feed.

The protein recovered from this invention is in a more concentrated form which increases its value as a protein source for both monogastric and ruminant animals. In addition the main protein in corn is Zein which has been used in the manufacture of a wide variety of commercial products, including coatings for paper cups, soda bottle cap linings, clothing fabric, buttons, adhesives, coatings and binders, recently this protein has been used as a coating for candy, nuts, fruit, pills, and other encapsulated foods and drugs. Additionally Zein can be further processed into resins and other bioplastic polymers.

The fibers recovered from the process of the present invention comprise mostly corn kernel fibers which can be used as raw materials for the production of lignocellulosic ethanol or butanol as well as other chemicals that use glucose and xylose as building blocks.

The present invention results in a significant reduction in energy needed for the grain ethanol co-product separation process and in reduction in the carbon intensity associated with production of grain based ethanol.

SUMMARY OF THE PRESENT INVENTION

It is the object of the present invention to separate a stream of whole stillage materials from ethanol production into a stream rich in fibers, a stream rich in oil, a stream rich in protein and fibers and a stream consisting of clean water that may be recycled in this process or used for various industrial purposes.

In one aspect of the present invention, a multi-stage substantially continuous process for separating a source stream, the source stream intermixedly containing fibers, water, protein and oil, the process being configured for separating the source stream into streams each containing predominantly one component, the process comprising the stages of: (a) providing a source stream comprising water, oil, protein and fibers; (b) separating the source stream into a fiber stream containing predominantly fibers and a first liquid fraction containing predominantly a mixture of water, oil and protein; and (c) separating the first liquid fraction into an oil stream containing predominantly oil, a protein stream comprising predominantly protein and an aqueous stream containing predominantly water, wherein step (b) is accomplished through the steps of: (A) adding dilution water to the source stream to produce a diluted source stream; (B) passing the diluted source stream through an oval plate separator, wherein actions of the oval plate separator result in separating the diluted source stream into a fiber slurry comprising predominantly fibers and into the first liquid fraction; and (C) passing the fiber slurry through a first press, wherein actions of the first press result in separating the fiber slurry into the fiber stream and a second liquid fraction containing predominantly a mixture of water, oil and protein.

In another aspect of the present invention, a multi-stage substantially continuous process for separating a source stream, the source stream intermixedly containing fibers, water, protein and oil, the process being configured for separating the source stream into streams each containing predominantly one component, the process comprising the stages of: (a) providing a source stream comprising water, oil, protein and fibers; (b) separating the source stream into a fiber stream containing predominantly fibers and a first liquid fraction containing predominantly a mixture of water, oil and protein; and (c) separating the first liquid fraction into an oil stream containing predominantly oil, a protein stream comprising predominantly protein and an aqueous stream containing predominantly water, wherein step (c) is accomplished by the steps of: (A) treating the first liquid fraction with at least about 5 ppm on a dry weight basis of anionic acrylamide copolymer, the treating being done through an addition at a first in-line port; (B) treating the first liquid fraction with at least about 5 ppm on a dry weight basis of cationic acrylamide copolymer, the treating being done through an addition at a second in-line port, the second in-line port being located at about 15 seconds after the first in-line port; (C) passing the first liquid fraction through a first dissolved air flotation device, wherein the actions of the first dissolved air flotation device result in separating the first liquid fraction into a non-aqueous fraction and an aqueous fraction, the non-aqueous fraction containing predominantly a mixture of water, oil and protein, the aqueous fraction containing predominantly water; (D) treating the non-aqueous fraction with a demulsifying composition to cause the protein to solidify, the demulsifying composition being added to the first liquid fraction at a rate of at least about 5 ppm on a dry weight basis; and (E) passing the non-aqueous fraction through a phase separator to separate out the oil stream, the protein stream and the aqueous stream.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention.

The first embodiment of the present invention includes the steps of:

1. Separating the whole stillage source stream containing water, fibers, non-aqueous liquids such as oil and protein into A) a stream containing predominantly water with between about 4%-10% non-aqueous solids that include protein, oil and fibers and B) a stream containing between 30-45% non-aqueous materials made of mostly fibers, and 2. Treating the stream containing predominantly water and 4-10% non-aqueous solids with a demulsifying composition that causes the protein to gel.

3. Separating the treated stream containing predominantly water with 4-10% non-aqueous solids into a stream containing predominantly water, a stream containing predominantly oil and a stream relatively rich in protein.

Figure 1:
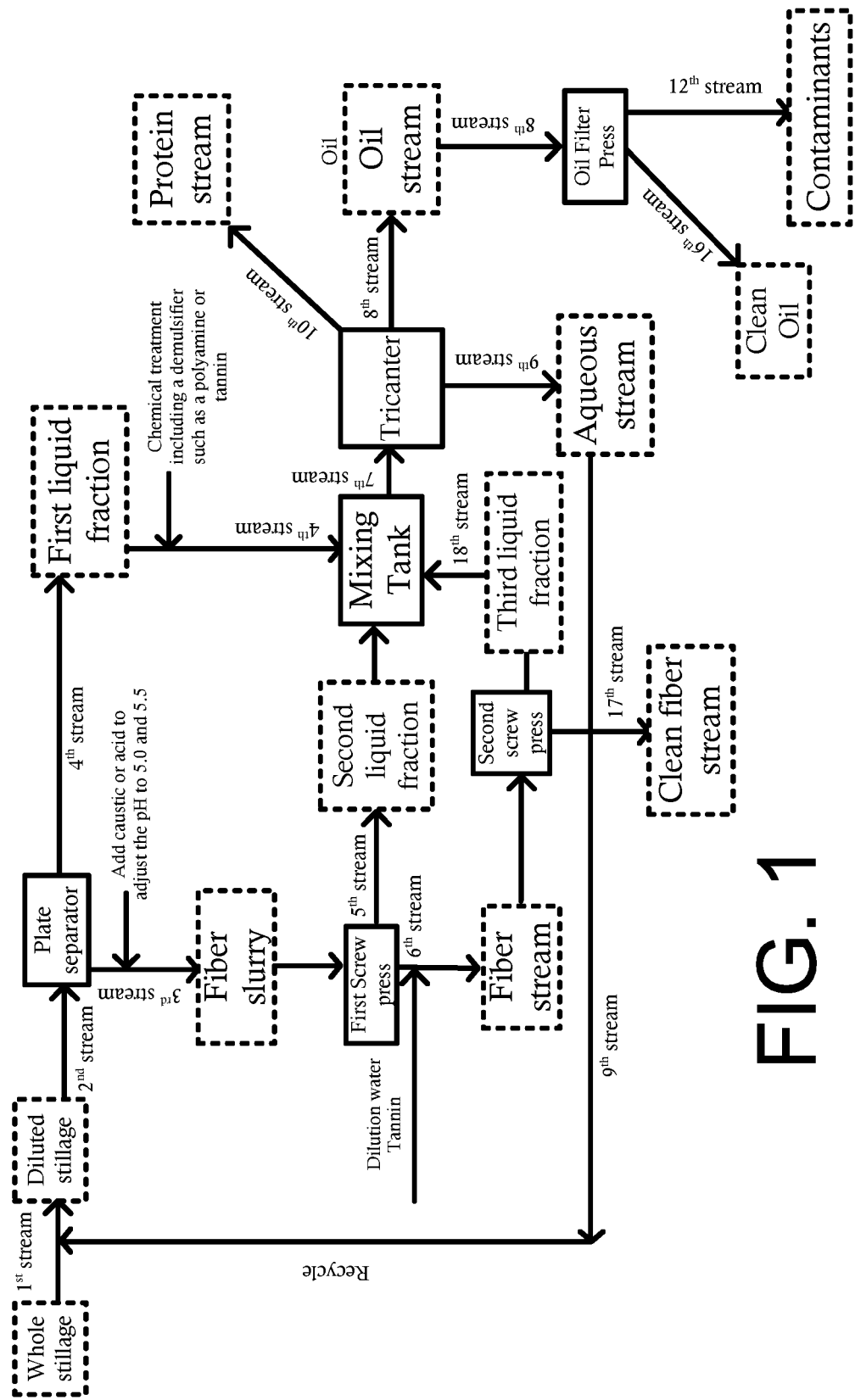
FIG. 1 is a flow chart schematic of the process according to an embodiment of the present invention.

FIG. 1 presents a flow chart of the first process embodiment. Each stream contains water and non-aqueous materials, also referred to as dry matter which can be solids or liquids. In this context, fibers are solid materials, while proteins and oil in their original form are non-aqueous liquids. Protein that is treated with a gelling composition generally turns into a thickened liquid or a solid. The gelling composition acts as a demulsifier and two compositions suitable for this purpose are polyamines and tannin.

The source stream labeled as the $1^{st}$ stream contains whole stillage from ethanol production and has dry matter in the range of about 10-20%. The $1^{st}$ stream is diluted with recycle water from the downstream process to about 6-12% solids. The dilute whole stillage, labeled as the $2^{nd}$ stream, is passed into a liquid-solid separator such as an oval plate separator or a combination of liquid-solid separators which separate the $2^{nd}$ stream into a $3^{rd}$ stream and a $4^{th}$ stream, labeled in FIG. 1 as the first liquid fraction. The $3^{rd}$ stream which contains predominantly fibers in a slurry form has a higher concentration of non-aqueous materials than the $2^{nd}$ stream while the $4^{th}$ stream has a lower concentration of non-aqueous materials than the $2^{nd}$ stream. A liquid-solid separator suitable for this application is an oval plate separator which functions to concentrate solids by passing them between rotating oval plates. An example of an oval plate separator currently being marketed commercially in the US is Trident KDS. However, other separators and combinations of separators also fall within the scope of the present invention.

The $3^{rd}$ stream is passed through a press to separate it into a $5^{th}$ stream and into a $6^{th}$ stream. In the $6^{th}$ stream, labeled in FIG. 1 as the fiber stream, the dry matter is further concentrated to contain between about 30% to about 45% dry matter, while in the $5^{th}$ stream, the dry matter is only in the range of about 7% to about 12%, thus it is significantly more dilute. The press maybe a screw press or another similar type of press suitable for this purpose.

The pH of the $3^{rd}$ stream may optionally be adjusted with either caustic (NaOH) or acid (e.g., nitric acid) to between about 5 and about 5.5. Acid would be used if the starting pH is higher than 5.5 while caustic or other base if the pH is lower than 5.0.

While dilute, the $4^{th}$ and $5^{th}$ streams contain significant amounts of dry materials that need to be recovered. The $4^{th}$ and $5^{th}$ streams are combined to form a $7^{th}$ stream which is passed through a phase separator. The $4^{th}$ stream is chemically treated with at least one composition that causes the protein to gel around the solid fibers to form a generally solid or semi-solid phase. Chemical compositions suitable as treatment chemicals for the $4^{th}$ stream include polyamine and tannin; however, other demulsifying compositions are also suitable for this treatment. Addition levels should be at least about 5 ppm and generally between about 5 ppm to about 25 ppm based on a dry composition of the stream. The gelling composition may be added in the $4^{th}$ stream in line or added into the mixing tank where the $4^{th}$ and $5^{th}$ streams are combined. In an embodiment of the present invention, the $7^{th}$ stream is heated to between about 150° F. to about 250° F. and, more preferably, to between about 200° F. to about 210° F. The heating may be accomplished by using a heat exchanger or by direct injection of steam into the stream. Heating the $7^{th}$ stream enhances the separation of the phases in the phase separator.

The phase separator is configured to separate three immiscible, but intermixed phases that contain a relatively low density liquid phase, a higher density liquid phase and a solid phase. The low density component in the $7^{th}$ stream is corn oil having a density of about 7.6 lb./gal. Water has a higher density at about 8.3 lb./gal. The gelled protein has a density of between about 10 to about 13 lb./gal.

A suitable phase separator to achieve the separation is a tricanter in which the contents of the stream are fed into a chamber under pressure. An impeller causes the heavy liquid to discharge at the top of the tricanter under pressure, the light liquid is discharged by gravity and a scroll carries the solids out from the liquid phases through a narrow discharge channel that allows passage of small solid particles and fragments.

The separated streams from the phase separator are the $8^{th}$ stream that contains over 95% oil, the $9^{th}$ stream that contains over 90% water and the $10^{th}$ stream that has a dry matter content of between 20% and 37% and is relatively rich in protein and fibers. Part of the $9^{th}$ stream may be used as dilution water for the whole stillage to form the $2^{nd}$ stream. The $8^{th}$ stream may be further passed through an oil filter to remove impurities from it. A suitable tricanter for this purpose is the Flottweg® tricanter that is currently available in the marketplace.

Table 1 below provides example composition ranges for the streams of the first embodiment process.

TABLE 1

First embodiment of the process

| Stream | Description | % Dry materials | % Protein | % Oil | % Fibers | Density, lb./gal |
|---|---|---|---|---|---|---|
| 1 | Whole stillage | 10-20 | 2-5 | 1-4 | 2-5 | 8.3 |
| 2 | Diluted stillage | 6-10 | 1-3 | 0.5-1.5 | 1-3 | 8.3 |
| 3 | Plate separator fiber fraction | 12-22 | 3-8 | 1-3 | 5-10 | 8.6 |
| 4 | Plate separator liquid fraction | 5-10 | 1-3 | 0.5-2.5 | <0.1 | 8.1 |
| 5 | Screw press liquid fraction | 7-12 | 1-3 | 0.5-2.5 | <0.1 | 8.1 |
| 6 | Screw press solid fraction | 30-45 | 8-14 | 2-4 | 20-25 | 9.0 |
| 7 | Tricanter feed | 4-8 | 1-2 | 0.5-1.5 | <0.1 | 8.1 |
| 8 | Tricanter oil fraction | 90-99 | 2-5 | 85-95 | 0.1-0.5 | 7.6 |
| 9 | Tricanter water fraction | 2-9 | 0.5-2 | 0.5-2 | <0.1 | 8.1 |
| 10 | Tricanter protein fraction | 20-37 | 10-17 | 2-6 | 5-14 | 10-13 |
| 11 | Filtered oil | 95-99 | 2-4 | 92-96 | <0.1 | 7.6 |

A screen analysis of the fibers present in the whole stillage (Stream 1) indicates that about 90% of the fibers are larger than 1.2 mm as they pass through a screen opening of about 1.2 mm.

If the fiber stream contains excessively high levels of protein, it may undergo several steps configured to remove the excess protein:

a. Diluting the fiber stream to between about 20-25% consistency using dilution water.
b. Treating the diluted fiber stream with at least about 5 ppm and generally about 5 ppm to about 15 ppm tannin on a dry basis of the diluted stream.
c. Feeding the treated dilute fiber ($6^{th}$) stream into a second press to generate a clean fiber stream, labeled as the $18^{th}$ stream, with lower levels of protein and a third liquid fraction, labeled as the $19^{th}$ stream, that is fed into the mixing tank preceding the tricanter.

Figure 2:
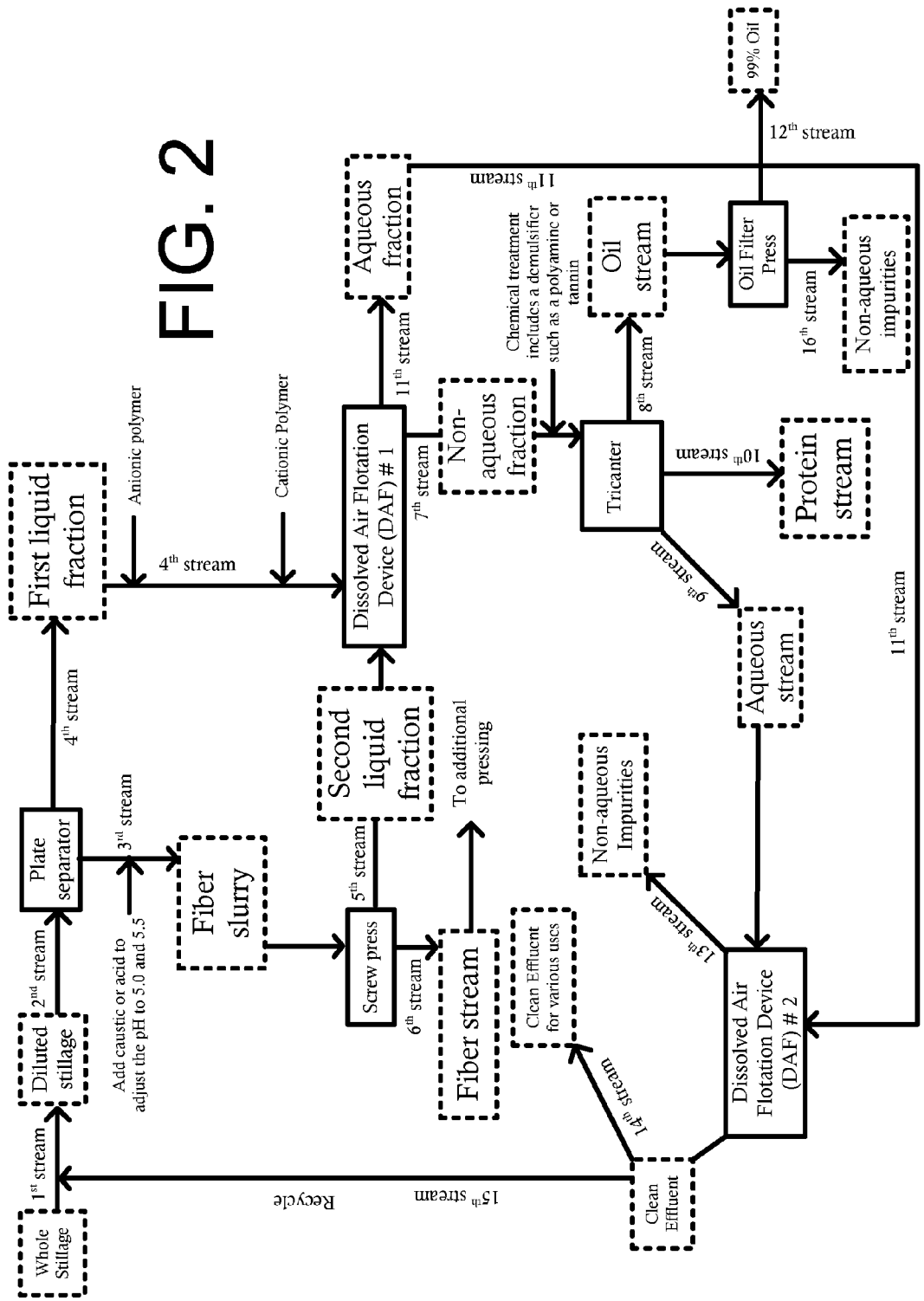
FIG. 2 is a flow chart schematic of the process according to another embodiment of the present invention.

The second embodiment of the present invention process is shown in FIG. 2. A dissolved air flotation device (DAF) is used to remove water from the $4^{th}$ stream prior to the separation in the tricanter. This allows for easier control over the process resulting in better consistency and reduced variability of the stream compositions. With the process configuration shown in FIG. 2, the $4^{th}$ and $5^{th}$ streams are fed into a first DAF (labeled as DAF #1) that separates out an $11^{th}$ stream that contains relatively low dry matter and a $7^{th}$ stream that contains most of the solids from the $4^{th}$ and $5^{th}$ streams. The $7^{th}$ stream is fed into the tricanter which separates it into three phases as was done in the first embodiment. The water from the tricanter in the $9^{th}$ stream may be combined with the water fraction from the DAF in the $11^{th}$ stream. The combination stream may further be passed through a second DAF (labeled as DAF #2) which removes additional dry matter from the water fraction. A portion of the water fraction from the second DAF, i.e., the $15^{th}$ stream, may be recycled to be used as dilution water for the whole stillage or for water to be used in the ethanol process. Reduction of the water content from the combined $4^{th}$ and $5^{th}$ streams using the first dissolved air flotation device (DAF) prior to feeding into the tricanter improves the operating efficiency of the tricanter.

As with the first embodiment, the $7^{th}$ stream entering into the phase separator is treated with a composition to cause the protein to gel around the fibers. The composition may be tannin or polyamine as in the first embodiment. This increases the density of the protein from about 9.0 lb./gal to between about 10 and 13 lb./gal. In this form, the protein is substantially a solid and may be effectively separated out by the phase separator.

Table 2 below provides example composition ranges of the streams for the second exemplary embodiment of the process.

TABLE 2

Second embodiment of the process

| Stream | Description | % Dry materials | % Protein | % Oil | % Fibers | Density, lb./gal |
|---|---|---|---|---|---|---|
| 1 | Whole stillage | 10-20 | 2-5 | 1-4 | 2-5 | 8.3 |
| 2 | Diluted stillage | 6-10 | 1-3 | 0.5-1.5 | 1-3 | 8.1 |
| 3 | Plate separator fiber fraction | 12-22 | 3-8 | 1-3 | 5-10 | 8.6 |
| 4 | Plate separator liquid fraction | 5-10 | 1-3 | 0.5-2.5 | <0.1 | 8.1 |
| 5 | Screw press liquid fraction | 7-12 | 1-3 | 0.5-2.5 | <0.1 | 8.1 |
| 6 | Screw press solid fraction | 30-45 | 8-14 | 2-4 | 20-25 | 9.0 |
| 7 | DAF solids fraction | 9-14 | 2-5 | 2-5 | 1-3 | 8.5 |
| 8 | Tricanter oil fraction | 95-99.9 | <0.1 | 95-99.9 | <0.1 | 7.6 |
| 9 | Tricanter water fraction | 2-4 | 0.5-1.5 | 0.5-1.5 | <0.1 | 8.1 |
| 10 | Tricanter protein fraction | 25-30 | 11-15 | 2-4 | 7-11 | 10-13 |
| 11 | DAF water fraction | 2-7 | 0.5-2 | 0.1-0.5 | <0.1 | 8.1 |
| 15 | Recycle water | 1-3 | 0.5-1 | 0.5-1 | <0.1 | 8.1 |

The $4^{th}$ and $5^{th}$ streams may be mixed before entering the first DAF and are treated with:

1. At least about 5 ppm and, generally, between about 5 ppm to about 100 ppm on a dry weight basis of an anionic acrylamide copolymer such as sodium or potassium acrylate acrylamide copolymer having a charge density of about 50% and a MW of between 18 million and 24 million, and
2. At least about 5 ppm and, generally, between about 5 ppm to about 100 ppm on a dry weight basis of an cationic acrylamide copolymer such as Acrylamide-dimethylaminoethyl acrylate copolymer (ADMAEA) having a Molecular Weight of between 8 million to 12 million and a charge density between about 20-40%.

The polymers are added in line at two addition points separated by 15 seconds calculated based on an average volumetric flow rate through the line. The anionic acrylamide copolymer is preferably added first. The additions of these polymers aids in the separation of the $4^{th}$ and $5^{th}$ streams that are fed into the first DAF into the $7^{th}$ and $11^{th}$ streams. The $7^{th}$ stream floats to the top of the first DAF and is removed as an overflow.

The $8^{th}$ stream containing over 95% oil in both the first and second embodiments may further be passed through an oil filter to remove impurities.

Below is information about the compositions and properties of the treatment chemicals added in the processes of the present invention:

Polyamines
  Molecular weight between 10,000 and 1,000,000
  Liquid form with 40 to 50% concentration
  Cationic site on the main chain
  Viscosity at 50% of between 40 and 20,000 centipoises.

Tannin
  Molecular weight between 10,000 and 300,000
  Liquid form with 30 to 40% concentration
  Cationic site on the main chain
  Viscosity at 50% of between 40 and 2000 centipoises
  Comes in various forms such as tannic acid $C_{17}H_{16}O_9$ and gallic acid $C_7H_6O_5$.

ADMAEA
  Acrylamide-dimethylaminoethyl acrylate copolymers.
  The copolymerization of DMAEA-MeCl with acrylamide produces the cationic polymer.
  The main characteristics of the products obtained are:
    Molecular weight: about 3 million to about 10 million.
  Viscosity at 5 g/l: 100 to 1700 cps.
  Specifically: acrylamide/Ethanaminium, N, N, N-trimethyl-2-((1-oxo-2-propenyl)oxo)-, chloride copolymer is a useful form of ADMAEA in the present invention.
  The molecular formula is $C_{11}H_{21}ClN_2O_3$. The molecular structure is shown below in 2D.

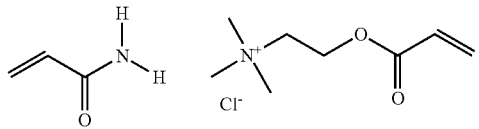

Cationic Acrylamide Copolymers

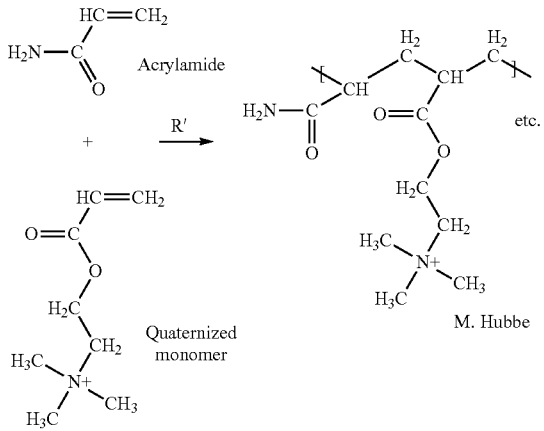

Sodium or Potassium Anionic Acrylate Acrylamide Copolymer.

This polymer may be made from the reaction between an acrylamide monomer and an acrylic acid monomer as shown below.

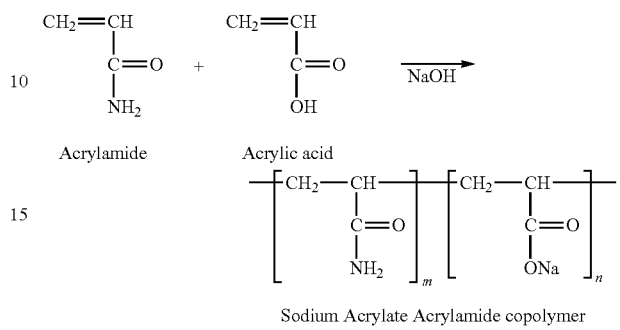

Sodium Acrylate Acrylamide copolymer

It is noted that a dry matter component, or a combination of several dry matter components, are defined, in the context of the present invention, as predominant in a given stream if they are present at a higher percentage than any of the other dry matter component in the stream.

It should be understood, of course, that the foregoing relates to exemplary embodiments of the invention and that modifications may be made without departing from the spirit and scope of the invention.

I claim:

1. A process for separating components of a source stream containing fibers, water, protein and oil, said process comprising:
   (a) passing a source stream comprising water, oil, protein and fibers through a plate separator producing a fiber slurry comprising predominantly fibers and a first liquid fraction comprising predominantly a mixture of water, oil, and protein;
   (b) separating the fiber slurry into a fiber stream and a second liquid fraction containing predominantly a mixture of water, oil and protein by pressing the fiber slurry with a first press;
   (c) separating the first liquid fraction into (i) an oil stream containing predominantly oil, (ii) a protein stream comprising predominantly protein, and (iii) an aqueous stream containing predominantly water, said separating the first liquid fraction comprises treating the first liquid fraction with a demulsifying composition to cause the protein to solidify, said demulsifying composition being added to the first liquid fraction at a level of about at least about 5 ppm on a dry weight basis.

2. The process of claim 1 wherein step (c) is accomplished by flowing the first liquid fraction through a tricanter, the protein stream is moved out a discharge opening of the tricanter by a scroll, the oil stream drains by gravity and the aqueous stream is discharged at a top of the tricanter under pressure by an impeller.

3. The process of claim 2, wherein said demulsifying composition is selected from at least one member of the group consisting of polyamine and tannin.

4. The process of claim 2, further comprising combining the first liquid fraction and the second liquid fraction and feeding the combined first liquid fraction and second liquid fraction into the tricanter.

5. The process of claim 1, further comprising adjusting the pH of the fiber slurry to about 5 to about 5.5.

6. The process of claim 2 further comprising:
(A) diluting the fiber stream until the fiber stream is about 20 percent to about 30 percent fiber to produce a diluted fiber stream;
(B) treating the diluted fiber stream with at least about 5 ppm tannin on a dry basis of the diluted fiber stream to produce a treated dilute fiber stream;
(C) passing the treated dilute fiber stream through a second press, said second press separating the treated dilute fiber stream into a clean fiber stream containing predominantly fibers and a third liquid fraction containing a mixture of water, oil and protein; and
(D) combining the third liquid fraction with the first liquid fraction and the second liquid fraction and feeding the combined first, second, and third liquid fractions into the tricanter.

7. A multi-stage substantially continuous process for separating a source stream containing fibers, water, protein and oil, said process comprising:
(a) providing a source stream comprising water, oil, protein and fibers;
(b) separating said source stream into a fiber stream containing predominantly fibers and a first liquid fraction containing predominantly a mixture of water, oil and protein; and
(c) separating the first liquid fraction into an oil stream containing predominantly oil, a protein stream comprising predominantly protein and an aqueous stream containing predominantly water,
wherein step (c) is accomplished by the steps of:
(A) treating the first liquid fraction with at least about 5 ppm on a dry weight basis of anionic acrylamide copolymer through a first port;
(B) treating the first liquid fraction with at least about 5 ppm on a dry weight basis of cationic acrylamide copolymer through a second port located downstream from the first port;
(C) passing the first liquid fraction through a first dissolved air flotation device resulting in separating the first liquid fraction into a non-aqueous fraction and an aqueous fraction, said non-aqueous fraction comprising predominantly a mixture of water, oil and protein, said aqueous fraction comprising predominantly water;
(D) treating the non-aqueous fraction with a demulsifying composition that causes the protein to solidify, said demulsifying composition being added to the first liquid fraction at a level of about at least about 5 ppm on a dry weight basis; and
(E) passing said non-aqueous fraction through a phase separator that phase separates the oil stream, the protein stream, and the aqueous stream.

8. The process of claim 7, wherein said demulsifying composition is selected from at least one member of the group consisting of polya mine and tannin.

9. The process of claim 7, wherein the phase separator is a tricanter in which the oil stream drains by gravity, the aqueous stream is discharged at a top of the tricanter by an impeller under pressure and the protein stream is moved out a discharge opening of the tricanter by a scroll.

10. The process of claim 7, further comprising feeding at least a portion of the aqueous fraction and the aqueous stream into a second dissolved air flotation device.

11. The process of claim 7, further comprising passing the oil stream through an oil press.

12. The process of claim 10, further comprising heating the non-aqueous fraction from about 150° F. to about 250° F.

13. The process of claim 10, further comprising heating the non-aqueous fraction from about 200° F. to about 210° F.

14. The process of claim 7 further comprising:
(F) diluting the fiber stream until the fiber stream is about 20 percent to about 30 percent fiber to produce a diluted fiber stream;
(G) treating the diluted fiber stream with at least about 5 ppm tannin to produce a treated dilute fiber stream;
(H) passing the treated dilute fiber stream through a press that separates the treated dilute fiber stream into a clean fiber stream containing predominantly fibers and a third liquid fraction containing a mixture of water, oil and protein; and
(I) combining the third liquid fraction with the non-aqueous fraction before feeding the non-aqueous fraction into the phase separator.

* * * * *